United States Patent [19]
Buettner

[11] Patent Number: 5,998,704
[45] Date of Patent: Dec. 7, 1999

[54] SOYBEAN CULTIVAR 9312069421822B

[75] Inventor: Mark John Buettner, Newburgh, Ind.

[73] Assignee: Monsanto Corporation, St. Louis, Mo.

[21] Appl. No.: 09/078,584

[22] Filed: May 14, 1998

[51] Int. Cl.$^6$ ................ A01H 5/00; A01H 5/10; A01H 1/02; C12N 5/04
[52] U.S. Cl. .................. 800/312; 800/260; 435/415
[58] Field of Search ...................... 800/312, 260; 435/415, 426, 430

Primary Examiner—Elizabeth F. McElwain
Attorney, Agent, or Firm—Rothwell, Figg, Ernst & Kurz

[57] ABSTRACT

A novel soybean cultivar, designated 9312069421822B, is disclosed. The invention relates to the seeds of soybean cultivar 9312069421822B, to the plants of soybean 9312069421822B and to methods for producing a soybean plant produced by crossing the cultivar 9312069421822B with itself or another soybean variety. The invention further relates to hybrid soybean seeds and plants produced by crossing the cultivar 9312069421822B with another soybean cultivar.

11 Claims, No Drawings

SOYBEAN CULTIVAR 9312069421822B

BACKGROUND OF THE INVENTION

The present invention relates to a new and distinctive soybean cultivar, designated 9312069421822B. There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety an improved combination of desirable traits from the parental germplasm. These important traits may include higher seed yield, resistance to diseases and insects, better stems and roots, tolerance to drought and heat, and better agronomic quality.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested and compared to appropriate standards in environments representative of the commercial target area(s) for three or more years. The best lines are candidates for new commercial cultivars; those still deficient in a few traits may be used as parents to produce new populations for further selection.

These processes, which lead to the final step of marketing and distribution, usually take from eight to 12 years from the time the first cross is made. Therefore, development of new cultivars is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

The goal of plant breeding is to develop new, unique and superior soybean cultivars and hybrids. The breeder initially selects and crosses two or more parental lines, followed by repeated selfing and selection, producing many new genetic combinations. The breeder can theoretically generate billions of different genetic combinations via crossing, selfing and mutations. The breeder has no direct control at the cellular level. Therefore, two breeders will never develop the same line, or even very similar lines, having the same soybean traits.

Each year, the plant breeder selects the germplasm to advance to the next generation. This germplasm is grown under unique and different geographical, climatic and soil conditions, and further selections are then made, during and at the end of the growing season. The cultivars which are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce the same cultivar twice by using the exact same original parents and the same selection techniques. This unpredictability results in the expenditure of large amounts of research monies to develop superior new soybean cultivars.

The development of new soybean cultivars requires the development and selection of soybean varieties, the crossing of these varieties and selection of superior hybrid crosses. The hybrid seed is produced by manual crosses between selected male-fertile parents or by using male sterility systems. These hybrids are selected for certain single gene traits such as pod color, flower color, pubescence color or herbicide resistance which indicate that the seed is truly a hybrid. Additional data on parental lines, as well as the phenotype of the hybrid, influence the breeder's decision whether to continue with the specific hybrid cross.

Pedigree breeding and recurrent selection breeding methods are used to develop cultivars from breeding populations. Breeding programs combine desirable traits from two or more cultivars or various broad-based sources into breeding pools from which cultivars are developed by selfing and selection of desired phenotypes. The new cultivars are evaluated to determine which have commercial potential.

Pedigree breeding is used commonly for the improvement of self-pollinating crops. Two parents which possess favorable, complementary traits are crossed to produce an $F_1$. An $F_2$ population is produced by selfing one or several $F_1$'s. Selection of the best individuals may begin in the $F_2$ population; then, beginning in the $F_3$, the best individuals in the best families are selected. Replicated testing of families can begin in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or inbred line which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

In a multiple-seed procedure, soybean breeders commonly harvest one or more pods from each plant in a population and thresh them together to form a bulk. Part of the bulk is used to plant the next generation and part is put in reserve. The procedure has been referred to as modified single-seed descent or the pod-bulk technique.

The multiple-seed procedure has been used to save labor at harvest. It is considerably faster to thresh pods with a machine than to remove one seed from each by hand for the single-seed procedure. The multiple-seed procedure also makes it possible to plant the same number of seeds of a population each generation of inbreeding. Enough seeds are harvested to make up for those plants that did not germinate or produce seed.

Descriptions of other breeding methods that are commonly used for different traits and crops can be found in one of several reference books (e.g., Allard, 1960; Simmonds, 1979; Sneep et al., 1979; Fehr, 1987).

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer; for special advertising and marketing, altered seed and commercial production practices, and new product utilization. The testing preceding release of a new cultivar should take into consideration research and development costs as well as technical superiority of the final cultivar. For seed-propagated cultivars, it must be feasible to produce seed easily and economically.

Soybean, *Glycine max* (L), is an important and valuable field crop. Thus, a continuing goal of plant breeders is to develop stable, high yielding soybean cultivars that are agronomically sound. The reasons for this goal are obviously to maximize the amount of grain produced on the land used and to supply food for both animals and humans. To accomplish this goal, the soybean breeder must select and develop soybean plants that have the traits that result in superior cultivars.

SUMMARY OF THE INVENTION

According to the invention, there is provided a novel soybean cultivar, designated 9312069421822B. This invention thus relates to the seeds of soybean cultivar 9312069421822B, to the plants of soybean 9312069421822B and to methods for producing a soybean plant produced by crossing the soybean 9312069421822B with itself or another soybean line.

DEFINITIONS

In the description and tables which follow, a number of terms are used. In order to provide a clear and consistent understanding of the specification and claims, including the scope to be given such terms, the following definitions are provided:

Maturity Date. Plants are considered mature when 95% of the pods have reached their mature color. The number of days are either calculated from September 1 or from the planting date.

Seed Yield (Bushels/Acre). The yield in bushels/acre is the actual yield of the grain at harvest.

Lodging Resistance. Lodging is rated on a scale of 1 to 5. A score of 1 indicates erect plants. A score of 2.5 indicates plants are leaning at a 45° angle in relation to the ground and a score of 5 indicates plants are laying on the ground.

Phytophthora Tolerance. Tolerance to Phytophthora root rot is rated on a scale of 1 to 5, with a score of 1 being the best or highest tolerance ranging down to a score of 5 which indicates the plants have no tolerance to Phytophthora.

Emergence. This score indicates the ability of the seed to emerge when planted 3" deep in sand and with a controlled temperature of 25° C. The number of plants that emerge each day are counted. Based on this data, each genotype is given a 1 to 5 score based on its rate of emergence and percent of emergence. A score of 1 indicates an excellent rate and percent of emergence, an intermediate score of 2.5 indicates average ratings and a 5 score indicates a very poor rate and percent of emergence.

Iron-Deficiency Chlorosis. Plants are scored 1 to 5 based on visual observations. A score of 1 means no stunting of the plants or yellowing of the leaves and a score of 5 indicates the plants are dead or dying caused by iron-deficiency chlorosis, a score of 2.5 means plants have intermediate health with some leaf yellowing.

Brown Stem Rot. This is a visual disease score from 1 to 5 comparing all genotypes in a given test. The score is based on leaf symptoms of yellowing and necrosis caused by brown stem rot. A score of 1 indicates no symptoms. Visual scores range to a score of 5 which indicates severe symptoms of leaf yellowing and necrosis.

Shattering. The amount of pod dehiscence prior to harvest. Pod dehiscence involves seeds falling from the pods to the soil. This is a visual score from 1 to 5 comparing all genotypes within a given test. A score of 1 means pods have not opened and no seeds have fallen out. A score of 2.5 indicates approximately 50% of the pods have opened, with seeds falling to the ground and a score of 5 indicates 100% of the pods are opened.

Plant Height. Plant height is taken from the top of soil to top node of the plant and is measured in inches.

Seed Protein Peroxidase Activity. Seed protein peroxidase activity is defined as a chemical taxonomic technique to separate cultivars based on the presence or absence of the peroxidase enzyme in the seed coat. There are two types of soybean cultivars, those having high peroxidase activity (dark red color) and those having low peroxidase activity (no color).

DETAILED DESCRIPTION OF THE INVENTION

Soybean cultivar 9312069421822B has superior characteristics and was developed from the cross A4539xA4341xA4138x40-3-2. $F_1$ and $F_2$ plants were advanced by a modified pedigree selection. $F_3$ derived $F_4$ lines were selected in 1995. In 1996 9312069421822B was entered in a yield test at 3 locations in the upper Midwest, where it placed third of 50 entries. In 1996, 9312069421822B was entered in a yield test at 9 locations in the upper Midwest, where it placed first of 40 entries.

9312069421822B is a mid maturity group IV variety with resistance to Roundup Ready™ herbicide. This variety has superior yield potential when compared to lines of similar maturity. 9312069421822B has excellent agronomic characteristics, including good lodging resistance. This variety is adapted to the mid group IV growing areas of the corn belt, including Illinois, Missouri and Indiana. It has a major gene for Phytophthora resistance, Rps1k, conferring resistance to most races of Phytophthora Root Rot.

Some of the criteria used to select in various generations include: seed yield, lodging resistance, emergence, disease tolerance, maturity, late season plant intactness, plant height and shattering resistance.

The cultivar has shown uniformity and stability for the traits, as described in the following variety description information. It has been self-pollinated a sufficient number of generations with careful attention to uniformity of plant type. The line has been increased with continued observation for uniformity.

Soybean cultivar 9312069421822B has the following morphologic and other characteristics (based primarily on data collected at Ridgway, Ill.).

VARIETY DESCRIPTION INFORMATION

1. Seed Coat Color: (Mature Seed)—Yellow
2. Seed Coat Luster: (Mature Hand Shelled Seed)—Dull
3. Hilum Color: (Mature Seed)—Black
4. Cotyledon Color: (Mature Seed)—Yellow
5. Seed Protein Peroxidase Activity: High
6. Hypocotyl Color: Green with bronze band below cotyledons
7. Leaflet Shape: Ovate
8. Flower Color: White
9. Pod Color: Tan
10. Plant Pubescence Color: Brown (Tawny)
11. Plant Type: Slender
12. Plant Habit: Indeterminate
13. Maturity Group: IV
14. Disease Reaction:

Phytophthora Rot (*Phytophthora megasperma* var. *sojae*):

| Race 1 | Resistant |
|---|---|
| Race 2 | Resistant |
| Race 3 | Resistant |
| Race 4 | Resistant |
| Race 5 | Resistant |
| Race 6 | Resistant |
| Race 7 | Resistant |
| Race 8 | Resistant |
| Race 9 | Resistant |

-continued

| Race 10 | Resistant |
|---|---|
| Race 11 | Resistant |
| Race 13 | Resistant |
| Race 14 | Resistant |
| Race 15 | Resistant |
| Race 17 | Resistant |
| Race 18 | Resistant |
| Race 22 | Resistant |
| Race 24 | Resistant |

Soybean Cyst Nematode (*Heterodera glycines*):

| Race 3 | Resistant |
|---|---|
| Race 14 | Susceptible |

15. Physiological Responses:

Roundup Ready herbicides: Resistant

16. Plant Lodging Score: 2.2

This invention is also directed to methods for producing a soybean plant by crossing a first parent soybean plant with a second parent soybean plant, wherein the first or second soybean plant is the soybean plant from the line 9312069421822B. Further, both first and second parent soybean plants may be from the cultivar 9312069421822B. Therefore, any methods using the cultivar 9312069421822B are part of this invention: selfing, backcrosses, hybrid breeding, and crosses to populations. Any plants produced using cultivar 9312069421822B as a parent are within the scope of this invention. As used herein, the term "plant" includes plant cells, plant protoplasts, plant cells of tissue culture from which soybean plants can be regenerated, plant calli, plant clumps, and plant cells that are intact in plants or parts of plants, such as pollen, flowers, seeds, pods, leaves, stems, and the like. Thus, another aspect of this invention is to provide for cells which upon growth and differentiation produce the cultivar 9312069421822B.

The cultivar 9312069421822B is similar to AG4501. While similar to AG4501, there are numerous differences including: AG4501 has the STS™ gene conferring tolerance to sulfyrnurea herbicides and 9312069421822B does not, and 9312069421822B is resistant to most races of Phytophthora Root Rot and AG4501 is susceptible to some races of that gene.

TABLES

In Tables 1, 2, and 3 that follow, the traits and characteristics of soybean cultivar 9312069421822B are compared to several competing varieties of commercial soybeans of similar maturity. In the table, column 1 shows the yield in bushels/acre for the instant invention and the Competitor Variety. Column 2 indicates the days to maturity after September 1 for the instant invention and the Competitor Variety. Column 3 shows the plant height in inches for the instant invention and the Competitor Variety. Column 4 indicates the plant lodging for the instant invention and the Competitor Variety. Column 5 shows the general rating scores for the instant invention and the Competitor Variety. Lodging and General Rating scores are rated 1=Best and 5=Worst.

TABLE 1

1995 YIELD DATA - LOCATIONS: IL, MD

|  | BU/A | MAT | HGT | LDG | GR |
|---|---|---|---|---|---|
| Overall Mean | 55.47 | 45.00 | 37.30 | 2.30 | 2.80 |
| Number of Locations | 3 | 3 | 2 | 2 | 3 |
| 9312069421822B | 61.61 | 44.00 | 37.50 | 3.00 | 3.70 |
| Asgrow A4401 | 58.29 | 46.00 | 39.00 | 2.50 | 2.30 |
| Asgrow A4138 | 57.55 | 40.30 | 36.00 | 2.50 | 2.70 |
| Asgrow A4715 | 50.71 | 48.00 | 33.00 | 2.00 | 2.70 |

TABLE 2

1996 YIELD DATA - LOCATIONS: IL, IN, MD, MO

|  | BU/A | MAT | HGT | LDG | GR |
|---|---|---|---|---|---|
| Overall Mean | 68.39 | 29.70 | 37.70 | 2.30 | 2.30 |
| Number of Locations | 9 | 8 | 7 | 8 | 8 |
| 9312069421822B | 73.06 | 30.40 | 39.00 | 2.90 | 3.20 |
| Asgrow A4341 | 70.75 | 28.50 | 34.90 | 1.90 | 2.20 |
| Asgrow A3834 | 69.64 | 26.50 | 30.80 | 1.50 | 1.40 |
| Asgrow A4138 | 69.10 | 26.90 | 38.40 | 2.70 | 3.10 |
| Asgrow AG4501 | 68.53 | 31.20 | 40.40 | 2.70 | 2.30 |

TABLE 3

1997 YIELD DATA - LOCATIONS: MD, MO, OH

|  | BU/A | MAT | HGT | LDG | GR |
|---|---|---|---|---|---|
| Overall Mean | 59.96 | 27.00 | 34.90 | 1.70 | 2.20 |
| Number of Locations | 17 | 11 | 11 | 11 | 11 |
| 9312069421822B | 63.49 | 27.80 | 35.20 | 2.20 | 2.80 |
| Asgrow A4341 | 62.87 | 26.90 | 32.60 | 1.30 | 2.00 |

TABLE 3-continued

1997 YIELD DATA - LOCATIONS: MD, MO, OH

|  | BU/A | MAT | HGT | LDG | GR |
|---|---|---|---|---|---|
| Asgrow A3834 | 62.68 | 25.60 | 30.00 | 1.20 | 1.40 |
| Asgrow A3904 | 62.55 | 23.40 | 35.10 | 1.80 | 1.80 |
| Pioneer P9421 | 61.43 | 30.20 | 33.10 | 1.60 | 2.50 |
| Pioneer P9452 | 61.40 | 22.50 | 29.90 | 1.90 | 2.60 |
| Dekalb CX445 | 61.22 | 26.80 | 36.70 | 1.90 | 2.60 |
| Dekalb CX434 | 61.22 | 26.20 | 34.10 | 1.50 | 2.40 |
| Asgrow A4138 | 61.05 | 24.30 | 35.20 | 2.50 | 3.10 |
| Asgrow AG4501 | 60.81 | 29.50 | 36.80 | 1.80 | 1.90 |
| Pioneer P9444 | 60.44 | 24.40 | 33.80 | 1.40 | 1.70 |

In Tables 4A and 4B, 5A and 5B, and 6A and 6B that follow, the traits and characteristics of soybean cultivar 9312069421822B are compared to several competing varieties of commercial soybeans of similar maturity. Each characteristic also indicates the number of locations which comprise the figures given. In these tables, column 1 shows the Competitor Variety. Columns 2 and 3 indicate the number of tests and years of testing. Columns 4, 5 and 6 indicate the yield in bushels/acre for the instant invention, the Competitor Variety identified in column 1 and the difference, respectively. Columns 8 and 9 indicate the days to maturity for the instant invention and Competitor Variety, respectively. Columns 12 and 13 show the plant lodging score of the instant invention and Competitor Variety. Columns 15 and 16 show the plant height in inches for the instant invention and the Competitor Variety respectively. Columns 18 and 19 show the general rating scores for the instant invention and the Competitor Variety, respectively. Lodging and General Rating scores are rated 1=Best and 5=Worst.

TABLE 4A

HEAD TO HEAD COMPARISONS OF 9312069421822B LISTED BELOW AS '1822-ALL YEARS-ALL LOCATIONS

| Other Variety or Hybrid | Loc. | Years | '1822 Yield Bu/A | Other Yield Bu/A | Diff | Loc. | '1822 Maturity >9/1 | Other Maturity >9/1 |
|---|---|---|---|---|---|---|---|---|
| Asgrow A3834 | 9 | 1 | 73.1 | 69.6 | 3.4 | 8 | 30.4 | 26.5 |
| Asgrow A4138 | 9 | 1 | 73.1 | 69.1 | 4.0 | 8 | 30.4 | 26.9 |
| Asgrow A4341 | 9 | 1 | 73.1 | 70.7 | 2.3 | 8 | 30.4 | 28.5 |
| Asgrow AG4501 | 9 | 1 | 73.1 | 68.5 | 4.5 | 8 | 30.4 | 31.2 |

TABLE 4B

CONTINUATION OF TABLE A

| Other Variety or Hybrid | Loc. | '1822 Lodge (1-9) | Other Lodge (1-9) | Loc. | '1822 Plt Hgt inches | Other Plt Hgt inches | Loc. | '1822 Gen Rtg (1-9) | Other Gen Rtg (1-9) |
|---|---|---|---|---|---|---|---|---|---|
| Asgrow A3834 | 8 | 2.9 | 1.5 | 7 | 39.0 | 30.8 | 8 | 3.2 | 1.4 |
| Asgrow A4138 | 8 | 2.9 | 2.7 | 7 | 39.0 | 38.4 | 8 | 3.2 | 3.1 |
| Asgrow A4341 | 8 | 2.9 | 1.9 | 7 | 39.0 | 34.9 | 8 | 3.2 | 2.2 |
| Asgrow AG4501 | 8 | 2.9 | 2.7 | 7 | 39.0 | 40.4 | 8 | 3.2 | 2.3 |

TABLE 5A

HEAD TO HEAD COMPARISONS OF 9312069421822B
LISTED BELOW AS '1822-ALL YEARS-LOCATIONS: MD

| Other Variety or Hybrid | Loc. | Years | '1822 Yield Bu/A | Other Yield Bu/A | Diff | Loc. | '1822 Maturity >9/1 | Other Maturity >9/1 |
|---|---|---|---|---|---|---|---|---|
| Asgrow A3834 | 3 | 1 | 71.1 | 73.5 | −2.4 | 3 | 27.3 | 23.7 |
| Asgrow A4138 | 3 | 1 | 71.1 | 72.8 | −1.7 | 3 | 27.3 | 23.2 |
| Asgrow A4341 | 3 | 1 | 71.1 | 71.1 | 0.0 | 3 | 27.3 | 25.2 |
| Asgrow AG4501 | 3 | 1 | 71.1 | 73.8 | −2.7 | 3 | 27.3 | 28.7 |

TABLE 5B

CONTINUATION OF TABLE A

| Other Variety or Hybrid | Loc. | '1822 Lodge (1–9) | Other Lodge (1–9) | Loc. | '1822 Plt Hgt inches | Other Plt Hgt inches | Loc. | '1822 Gen Rtg (1–9) | Other Gen Rtg (1–9) |
|---|---|---|---|---|---|---|---|---|---|
| Asgrow A3834 | 3 | 3.5 | 1.6 | 2 | 38.0 | 30.0 | 3 | 3.7 | 1.3 |
| Asgrow A4138 | 3 | 3.5 | 3.2 | 2 | 38.0 | 35.8 | 3 | 3.7 | 3.3 |
| Asgrow A4341 | 3 | 3.5 | 2.1 | 2 | 38.0 | 32.8 | 3 | 3.7 | 2.0 |
| Asgrow AG4501 | 3 | 3.5 | 3.0 | 2 | 38.0 | 40.8 | 3 | 3.7 | 2.8 |

TABLE 6A

HEAD TO HEAD COMPARISONS OF 9312069421822B
LISTED BELOW AS '1822-ALL YEARS-LOCATIONS: IL, IN

| Other Variety or Hybrid | Loc. | Years | '1822 Yield Bu/A | Other Yield Bu/A | Diff | Loc. | '1822 Maturity >9/1 | Other Maturity >9/1 |
|---|---|---|---|---|---|---|---|---|
| Asgrow A3834 | 5 | 1 | 74.4 | 69.4 | 5.0 | 5 | 32.3 | 28.3 |
| Asgrow A4138 | 5 | 1 | 74.4 | 68.8 | 5.6 | 5 | 32.3 | 29.2 |
| Asgrow A4341 | 5 | 1 | 74.4 | 71.4 | 3.0 | 5 | 32.3 | 30.5 |
| Asgrow AG4501 | 5 | 1 | 74.4 | 67.1 | 7.3 | 5 | 32.3 | 32.7 |

TABLE 6B

CONTINUATION OF TABLE A

| Other Variety or Hybrid | Loc. | '1822 Lodge (1–9) | Other Lodge (1–9) | Loc. | '1822 Plt Hgt inches | Other Plt Hgt inches | Loc. | '1822 Gen Rtg (1–9) | Other Gen Rtg (1–9) |
|---|---|---|---|---|---|---|---|---|---|
| Asgrow A3834 | 5 | 2.5 | 1.4 | 5 | 39.4 | 31.2 | 5 | 2.9 | 1.4 |
| Asgrow A4138 | 5 | 2.5 | 2.4 | 5 | 39.4 | 39.4 | 5 | 2.9 | 3.0 |
| Asgrow A4341 | 5 | 2.5 | 1.7 | 5 | 39.4 | 35.7 | 5 | 2.9 | 2.2 |
| Asgrow AG4501 | 5 | 2.5 | 2.4 | 5 | 39.4 | 40.2 | 5 | 2.9 | 2.0 |

DEPOSIT INFORMATION

A deposit of the soybean seed of this invention is maintained by Asgrow Seed Company, 4140 114th Street, Urbandale, Iowa 50322. Access to this deposit will be available during the pendency of this application to persons determined by the Commissioner of Patents and Trademarks to be entitled thereto under 37 CFR 1.14 and 35 USC 122. Upon allowance of any claims in this application, all restrictions on the availability to the public of the variety will be irrevocably removed by affording access to a deposit of at least 2,500 seeds of the same variety with the American Type Culture Collection, Manassas, Va.

Although the foregoing invention has been described in some detail by way of illustration and example for purposes of clarity and understanding, it will be obvious that certain changes and modifications may be practiced within the scope of the invention, as limited only by the scope of the appended claims.

What is claimed is:

1. A soybean seed designated 9312069421822B and having ATCC Accession No. PTA-273.
2. A plant or its parts produced by growing the seed of claim 1.
3. Pollen of the plant of claim 2.
4. An ovule of the plant of claim 2.
5. A soybean plant having all of the physiological and morphological characteristics of the soybean plant of claim 2.
6. Tissue culture of the plant of claim 2.
7. A soybean plant regenerated from the tissue culture of claim 6 wherein the regenerated soybean plant has all of the physiological and morphological characteristics of a plant grown from a soybean seed designated 9312069421822B.

8. A method for producing a hybrid soybean seed comprising crossing a first parent soybean plant with a second parent soybean plant and harvesting the resultant hybrid soybean seed, wherein said first or second parent soybean plant is the soybean plant of claim 2.

9. A hybrid seed produced by the method of claim 8.

10. A hybrid plant or its parts produced by growing said hybrid soybean seed of claim 9.

11. Seed produced from said hybrid plant of claim 10.

* * * * *